(12) United States Patent
Donhowe et al.

(10) Patent No.: US 9,429,696 B2
(45) Date of Patent: Aug. 30, 2016

(54) SYSTEMS AND METHODS FOR REDUCING MEASUREMENT ERROR IN OPTICAL FIBER SHAPE SENSORS

(71) Applicant: Intuitive Surgical Operations, Inc., Sunnyvale, CA (US)

(72) Inventors: Caitlin Q. Donhowe, Sunnyvale, CA (US); Stephen J. Blumenkranz, Redwood City, CA (US); Vincent Duindam, Mountain View, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 385 days.

(21) Appl. No.: 13/925,965

(22) Filed: Jun. 25, 2013

(65) Prior Publication Data

US 2013/0345719 A1    Dec. 26, 2013

Related U.S. Application Data

(60) Provisional application No. 61/663,951, filed on Jun. 25, 2012.

(51) Int. Cl.
| | | |
|---|---|---|
| *A61B 19/00* | (2006.01) | |
| *G02B 6/00* | (2006.01) | |
| *A61B 1/00* | (2006.01) | |
| *A61B 18/00* | (2006.01) | |

(52) U.S. Cl.
CPC .............. *G02B 6/00* (2013.01); *A61B 1/00165* (2013.01); *A61B 1/00167* (2013.01); *A61B 90/06* (2016.02); *A61B 2018/00791* (2013.01)

(58) Field of Classification Search
CPC ................. A61B 2018/00791; A61B 1/00165; A61B 1/00167; A61B 90/06; G02B 6/00
See application file for complete search history.

(56) References Cited

U.S. PATENT DOCUMENTS

| | | | |
|---|---|---|---|
| 5,404,743 | A | 4/1995 | Froggatt |
| 5,771,204 | A | 6/1998 | Froggatt |
| 5,798,521 | A | 8/1998 | Froggatt |
| 5,841,032 | A | 11/1998 | Froggatt |
| 6,376,830 | B1 | 4/2002 | Froggatt et al. |
| 6,389,187 | B1 | 5/2002 | Greenaway et al. |
| 6,426,496 | B1 | 7/2002 | Froggatt et al. |
| 6,545,760 | B1 | 4/2003 | Froggatt et al. |
| 6,566,648 | B1 | 5/2003 | Froggatt |
| 6,856,400 | B1 | 2/2005 | Froggatt |
| 6,900,897 | B2 | 5/2005 | Froggatt |
| 7,042,573 | B2 | 5/2006 | Froggatt |
| 7,330,245 | B2 | 2/2008 | Froggatt |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Ruth S Smith

(57) ABSTRACT

A shape sensing apparatus comprises an instrument including an elongated shaft with a neutral axis. The shape sensing apparatus also includes a first shape sensor with an elongated optical fiber extending within the elongated shaft at a first radial distance from the neutral axis. The apparatus also includes a shape sensor compensation device extending within the elongated shaft. The apparatus also comprises a tracking system for receiving shape data from the first shape sensor and compensating data from the shape sensor compensation device for use in calculating a bend measurement for the instrument.

7 Claims, 7 Drawing Sheets

(56) References Cited

U.S. PATENT DOCUMENTS

| | | |
|---|---|---|
| 7,379,168 B2 | 5/2008 | Froggatt et al. |
| 7,388,673 B2 | 6/2008 | Froggatt et al. |
| 7,440,087 B2 | 10/2008 | Froggatt et al. |
| 7,515,276 B2 | 4/2009 | Froggatt et al. |
| 7,538,883 B2 | 5/2009 | Froggatt |
| 7,633,607 B2 | 12/2009 | Froggatt et al. |
| 7,720,322 B2 | 5/2010 | Prisco |
| 7,772,541 B2 | 8/2010 | Froggatt et al. |
| 7,781,724 B2 | 8/2010 | Childers et al. |
| 7,930,065 B2 | 4/2011 | Larkin et al. |
| 7,948,633 B2 | 5/2011 | Froggatt et al. |
| 8,004,686 B2 | 8/2011 | Froggatt et al. |
| 8,400,620 B2 | 3/2013 | Froggatt et al. |
| 8,531,655 B2 | 9/2013 | Klein et al. |
| 8,537,367 B2 | 9/2013 | Froggatt |
| 8,714,026 B2 | 5/2014 | Froggatt et al. |
| 8,773,650 B2 | 7/2014 | Froggatt et al. |
| 2006/0013523 A1 | 1/2006 | Childlers et al. |
| 2010/0202727 A1 | 8/2010 | Prisco et al. |
| 2011/0202069 A1 | 8/2011 | Prisco et al. |
| 2011/0224825 A1 | 9/2011 | Larkin et al. |
| 2012/0277531 A1* | 11/2012 | Krattiger .......... G01B 7/18 600/117 |
| 2012/0289777 A1 | 11/2012 | Chopra et al. |

* cited by examiner

SYSTEMS AND METHODS FOR REDUCING MEASUREMENT ERROR IN OPTICAL FIBER SHAPE SENSORS

CROSS-REFERENCE TO RELATED APPLICATIONS

This application claims the benefit of U.S. Provisional Application 61/663,951 filed Jun. 25, 2012, which is incorporated by reference herein in its entirety.

FIELD

The present disclosure is directed to systems and methods for reducing measurement error in a shape sensing optical fiber, and more particularly to systems and methods for reducing measurement error in shape sensing optical fibers used in surgical instruments.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created passageways in anatomical systems such as the lungs, the colon, the intestines, the kidneys, the heart, the circulatory system, or the like. Navigational assist systems help the clinician route the surgical instruments and avoid damage to the anatomy. These systems can incorporate the use of shape sensors to more accurately describe the shape, position, orientation, and pose of the surgical instrument in real space or with respect to pre-procedural or concurrent images. The accuracy and precision of these shape sensors may be compromised by many factors including temperature variations, the location of the shape sensor within the instrument, and axial loading on the sensor. Improved systems and methods are needed for increasing the accuracy and precision of navigational assist systems, including minimizing the effects of factors that compromise shape sensor accuracy.

SUMMARY

The embodiments of the invention are summarized by the claims that follow below.

In one embodiment, a shape sensing apparatus comprises an instrument including an elongated shaft with a neutral axis. The shape sensing apparatus also includes a first shape sensor with an elongated optical fiber generally parallel to and at a first radial distance from the neutral axis of the elongated shaft. The apparatus also includes a shape sensor compensation device extending within the elongated shaft parallel to the neutral axis. The apparatus also comprises a tracking system for receiving shape data from the first shape sensor and compensating data from the shape sensor compensation device for use in calculating a bend measurement for the instrument.

In another embodiment, a shape sensing method comprises providing an instrument including an elongated shaft defining a neutral axis. The method also comprises receiving shape data from a first shape sensor. The first shape sensor includes an elongated optical fiber extending within the elongated shaft parallel to and at a first radial distance from the neutral axis. The method also comprises receiving compensation data from a shape sensor compensation device aligned with the elongated shaft parallel to the neutral axis. The method also comprises generating an instrument bend measurement based upon the received shape data and the compensation data.

In another embodiment, a medical instrument system comprises a surgical instrument with an elongated shaft having a neutral axis. The system also includes a first shape sensor including an elongated optical fiber extending within the elongated shaft parallel to and at a first radial distance from the neutral axis. The system further includes a shape sensor compensation device extending within the elongated shaft parallel to the neutral axis. The system further includes a tracking system adapted to receive shape data from the first shape sensor and compensating data from the shape sensor compensation device for calculating a bend measurement for the instrument. The system further includes a display system for displaying a virtual image of the surgical instrument using the bend measurement.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X,Y,Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
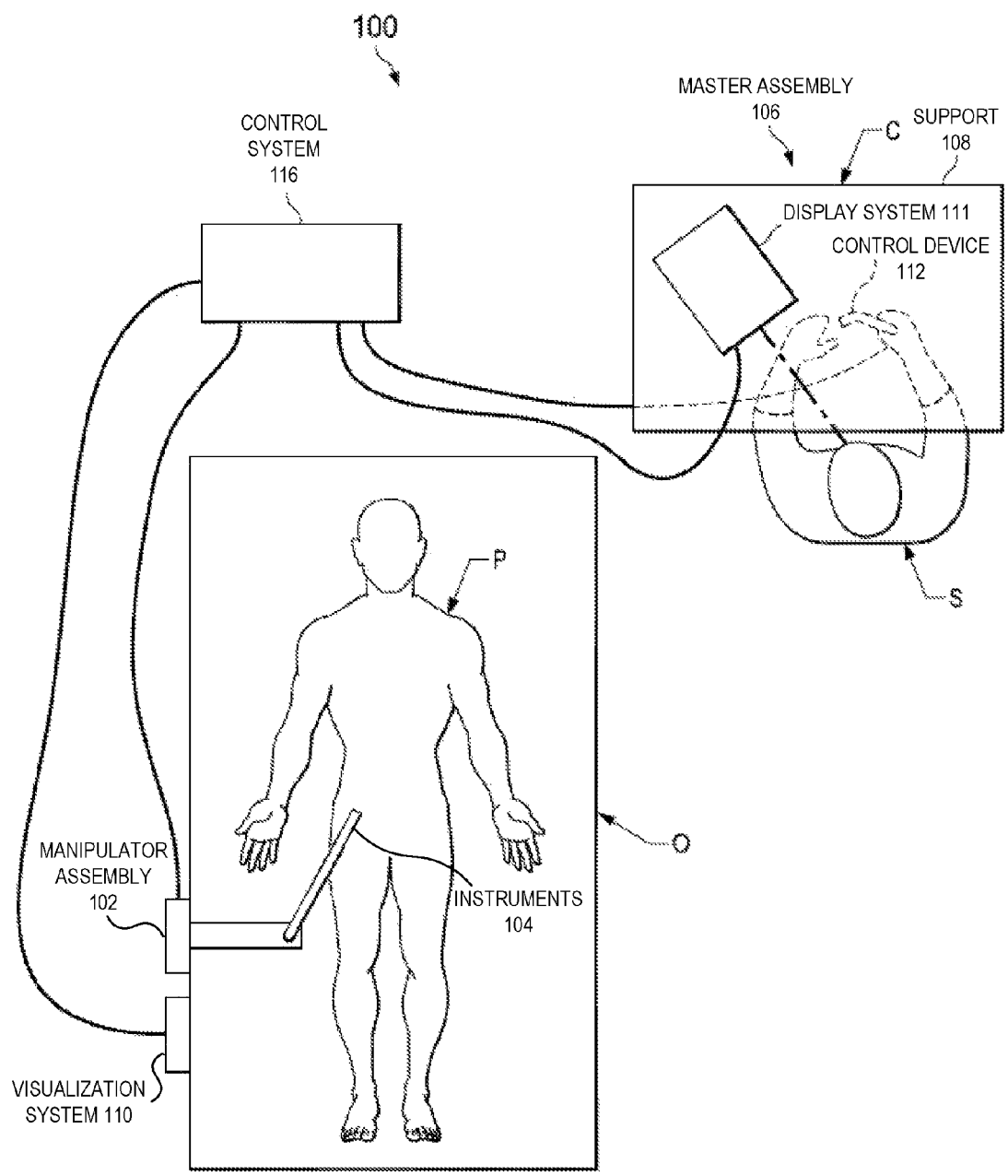
FIG. 1 is a robotic surgical system, in accordance with embodiments of the present disclosure.

Referring to FIG. 1 of the drawings, a robotic surgical system is generally indicated by the reference numeral 100. As shown in FIG. 1, the robotic system 100 generally includes a surgical manipulator assembly 102 for operating a surgical instrument 104 in performing various procedures on the patient P. The assembly 102 is mounted to or near an operating table O. A master assembly 106 allows the surgeon S to view the surgical site and to control the manipulator assembly 102.

In alternative embodiments, the robotic system may include more than one manipulator assembly. The exact number of manipulator assemblies will depend on the surgical procedure and the space constraints within the operating room among other factors.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, gloves, trigger-guns, hand-operated controllers, voice recognition devices or the like. In some embodiments, the control device(s) 112 will be provided with the same degrees of freedom as the associated surgical instruments 104 to provide the surgeon with telepresence, or the perception that the control device(s) 112 are integral with the instruments 104 so that the surgeon has a strong sense of directly controlling instruments 104. In some embodiments, the control devices 112 are manual input devices which move with six degrees of freedom, and which may also include an actuatable handle for actuating instruments (for example, for closing grasping jaws, applying an electrical potential to an electrode, delivering a medicinal treatment, or the like).

A visualization system 110 may include a viewing scope assembly (described in greater detail below) such that a concurrent or real-time image of the surgical site is provided to surgeon console C. The concurrent image may be, for example, a two or three dimensional image captured by an endoscope positioned within the surgical site. In this embodiment, the visualization system 110 includes endoscopic components that may be integrally or removably coupled to the surgical instrument 104. However in alternative embodiments, a separate endoscope, attached to a separate manipulator assembly may be used with the surgical instrument to image the surgical site. The visualization system 110 may be implemented as hardware, firmware, software or a combination thereof which interact with or are otherwise executed by one or more computer processors, which may include the processors of a control system 116 (described below).

A display system 111 may display an image of the surgical site and surgical instruments captured by the visualization system 110. The display 111 and the master control devices 112 may be oriented such that the relative positions of the imaging device in the scope assembly and the surgical instruments are similar to the relative positions of the surgeon's eyes and hands so the operator can manipulate the surgical instrument 104 and the hand control as if viewing the workspace in substantially true presence. By true presence, it is meant that the presentation of an image is a true perspective image simulating the viewpoint of an operator that is physically manipulating the surgical instruments 104.

Alternatively or additionally, monitor 111 may present images of the surgical site recorded and/or modeled preoperatively using imaging technology such as, computerized tomography (CT), magnetic resonance imaging (MRI), fluoroscopy, thermography, ultrasound, optical coherence tomography (OCT), thermal imaging, impedence imaging, laser imaging, or nanotube X-ray imaging. In some embodiments, the monitor 111 may display a virtual navigational image in which the actual location of the surgical instrument is dynamically referenced with preoperative images to present the surgeon S with a virtual image of the surgical site at the location of the tip of the surgical instrument. An image of the tip of the surgical instrument or other graphical or alphanumeric indicators may be superimposed on the virtual image to assist the surgeon controlling the surgical instrument.

As shown in FIG. 1, a control system 116 includes at least one processor and typically a plurality of processors for effecting control between the surgical manipulator assembly 102, the master assembly 106, and the image and display system 110. The control system 116 also includes software programming instructions to implement some or all of the methods described herein. While control system 116 is shown as a single block in the simplified schematic of FIG. 1, the system may comprise a number of data processing circuits (e.g., on the surgical manipulator assembly 102 and/or on the master assembly 106), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system 116 may support wireless communication protocols such as Bluetooth, IrDA, HomeRF, IEEE 802.11, DECT, and Wireless Telemetry.

In some embodiments, control system 116 may include servo controllers to provide force and torque feedback from the surgical instruments 104 to the hand-operated control device 112. Any suitable conventional or specialized servo controller may be used. A servo controller may be separate from, or integral with manipulator assemblies 102. In some embodiments, the servo controller and manipulator assembly are provided as part of a robotic arm cart positioned adjacent to the patient's body. The servo controller transmits signals instructing the manipulator assemblies to move instruments which extend into an internal surgical site within the patient body via openings in the body.

Each of the manipulator assemblies 102 that support a surgical instrument 104 and may comprise a series of manually articulatable linkages, generally referred to as set-up joints, and a robotic manipulator. The robotic manipulator assemblies 102 may be driven by a series of actuators (e.g., motors). These motors actively move the robotic manipulators in response to commands from the control system 116. The motors are further coupled to the surgical instrument so as to advance the surgical instrument into a naturally or surgically created anatomical orifice and to move the distal end of the surgical instrument in multiple degrees of freedom that may include three degrees of linear motion (e.g., X, Y, Z linear motion) and three degrees of rotational motion (e.g., roll, pitch, yaw). Additionally, the motors can be used to actuate an articulatable end effector of the instrument for grasping tissues in the jaws of a biopsy device or the like.

Figure 2:
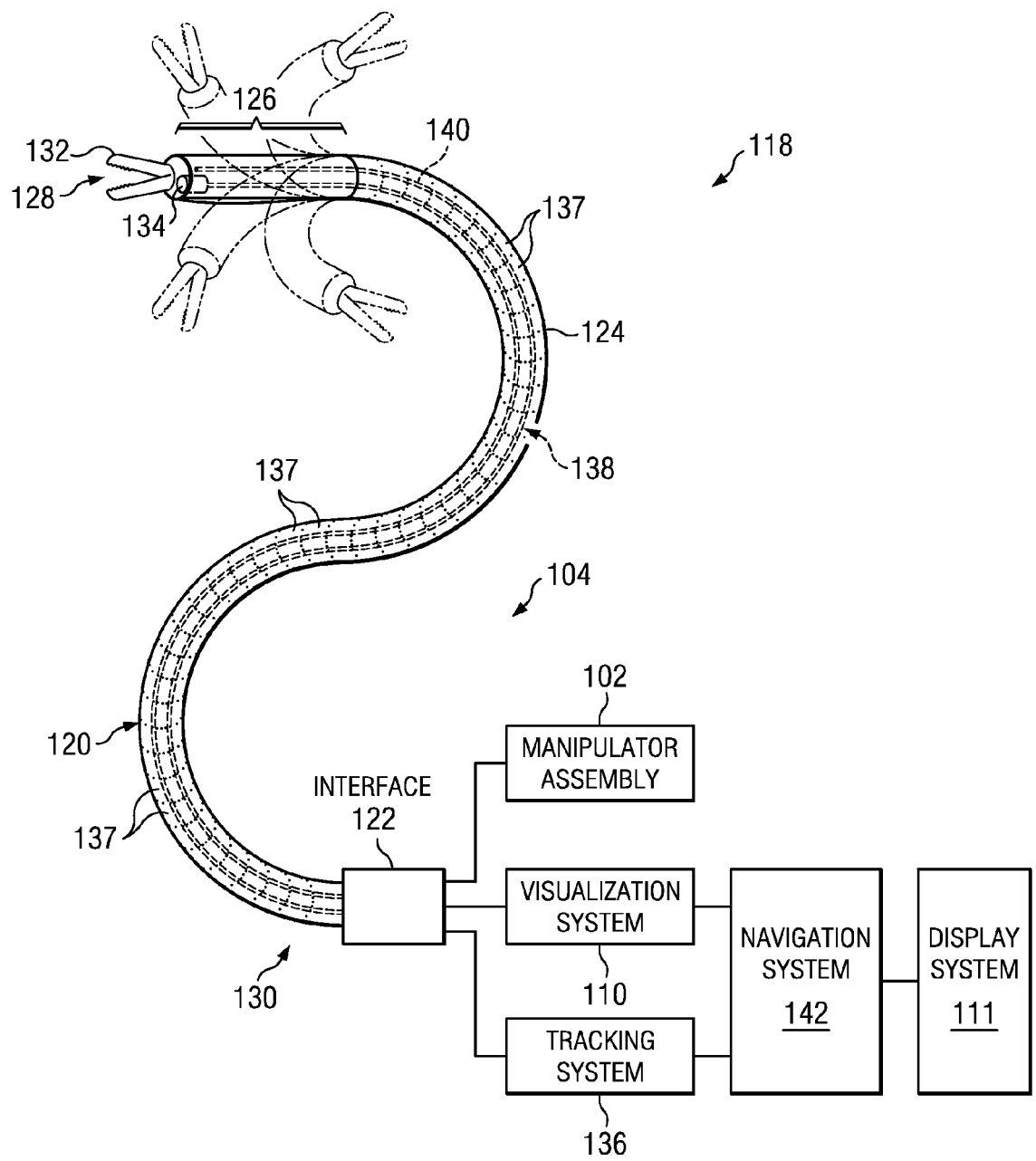
FIG. 2 illustrates a surgical instrument system utilizing aspects of the present disclosure

FIG. 2 illustrates a shape sensing apparatus 118 which includes the surgical instrument system 104 and its interfacing systems. The surgical instrument system 104 includes a steerable instrument 120 coupled by an interface 122 to manipulator assembly 102 and visualization system 110. The instrument 120 has a flexible body 124, a steerable tip 126 at its distal end 128, and the interface 122 at its proximal end 130. The body 124 houses cables, linkages, or other steering controls (not shown) that extend between the interface 122 and the tip 126 to controllably bend or turn the tip as shown for example by the dotted line versions of the bent tip 126, and in some embodiments control an optional end effector 132. The end effector is a working distal part that is manipulable for a medical function, e.g., for effecting a predetermined treatment of a target tissue. For instance, some end effectors have a single working member such as a scalpel, a blade, or an electrode. Other end effectors such as the embodiment of FIG. 2, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, treatments requiring fluid delivery, accessory introduction, biopsy extraction and the like). In other embodiments, flexible body 124 can define one or more lumens through which surgical instruments can be deployed and used at a target surgical location.

The instrument 120 can also include an image capture element 134 which may include a stereoscopic or monoscopic camera disposed at the distal end 128 for capturing images that are transmitted to and processed by the visualization system 110 for display by the display system 111. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum.

A tracking system 136 interfaces with a sensor system 138 for determining the shape (and optionally, pose) of the distal end 128 and or one or more segments 137 along the instrument 120. Although only an exemplary set of segments 137 are depicted in FIG. 2, the entire length of the instrument 120, between the distal end 128 and the proximal end 130 and including the tip 126 may be effectively divided into segments, the shape (and location, pose, and/or position) of which may be determined by the sensor system 138. The tracking system 136 may be implemented as hardware, firmware, software or a combination thereof which interact with or are otherwise executed by one or more computer processors, which may include the processors of a control system 116.

The sensor system 138 includes an optical fiber 140 aligned with the flexible body 124 (e.g., provided within an interior channel (not shown) or mounted externally). The tracking system 136 is coupled to a proximal end of the optical fiber 140. In this embodiment, the fiber 140 has a diameter of approximately 200 µm. In other embodiments, the dimensions may be larger or smaller.

The optical fiber 140 forms a fiber optic bend sensor for determining the shape of the instrument 120. In one alternative, optical fibers including Fiber Bragg Gratings (FBG) are used to provide strain measurements in structures in one or more dimensions. Various systems and methods for monitoring the shape and relative position of a optical fiber in three dimensions are described in U.S. patent application publication no. 2006/0013523, filed on Jul. 13, 2005, U.S. provisional patent application Ser. No. 60/588,336, filed on Jul. 16, 2004, and U.S. Pat. No. 6,389,187, filed on Jun. 17, 1998, the disclosures of which are incorporated herein in their entireties. In other alternatives, sensors employing other strain sensing techniques such as Rayleigh scattering, Raman scattering, Brillouin scattering, and Fluorescence scattering may be suitable. In other alternative embodiments, the shape of the instrument 120 may be determined using other techniques. For example, if the history of instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument. Alternatively, a series of positional sensors, such as electromagnetic (EM) sensors, positioned along the instrument can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

The optical fiber 140 is used to monitor the shape of at least a portion of the instrument 120. More specifically, light passing through the optical fiber 140 is processed by the tracking system 126 for detecting the shape of the surgical instrument 120 and for utilizing that information to assist in surgical procedures. The tracking system 136 may include a detection system for generating and detecting the light used for determining the shape of the instrument 120. This information, in turn, in can be used to determine other related variables, such as velocity and acceleration of the parts of a surgical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

The information from the tracking system 136 may be sent to the navigation system 142 where it is combined with information from the visualization system 110 and/or the preoperatively taken images to provide the surgeon or other operator with real-time position information on the display system 111 for use in the control of the instrument 120. The control system 116 may utilize the position information as feedback for positioning the instrument 120. Various systems for using fiber optic sensors to register and display a surgical instrument with surgical images are provided in U.S. patent application Ser. No. 13/107,562, entitled "Medical System Providing Dynamic Registration of a Model of an Anatomical Structure for Image-Guided Surgery," which is incorporated by reference herein in its entirety.

In the embodiment of FIG. 2, the instrument 104 is teleoperated within the robotic surgical system 100. In an alternative embodiment, the manipulator assembly may be replaced by direct operator control. In the direct operation alternative, various handles and operator interfaces may be included for hand-held operation of the instrument.

Figure 3:
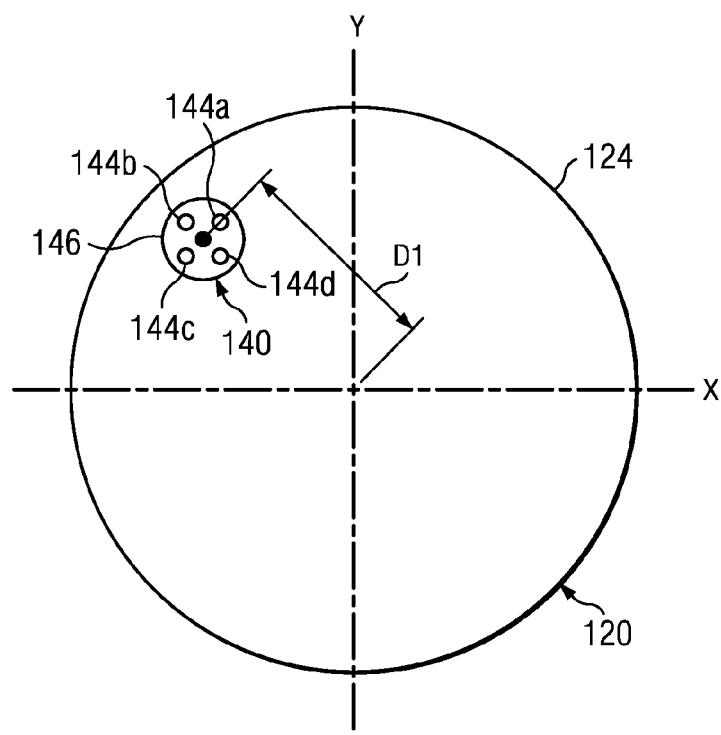
FIGS. 3 and 4 are cross-sectional views of a surgical instrument including an optical fiber shape sensor according to one embodiment of the present disclosure.
Figure 4:
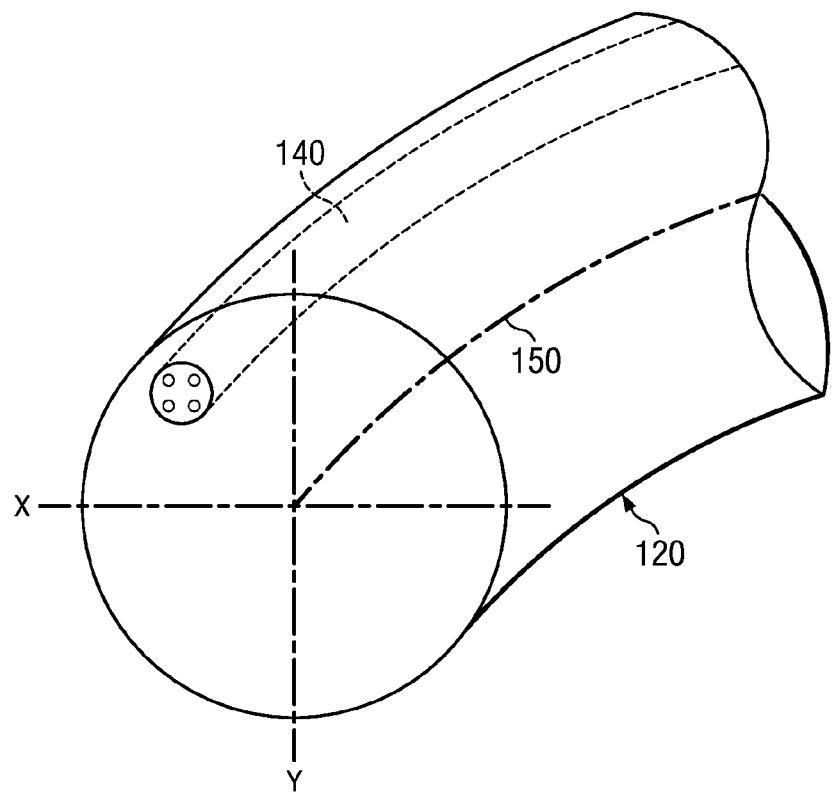

FIGS. 3 and 4 are cross-sectional views of the surgical instrument 120 including the optical fiber shape sensor 140 according to one embodiment of the present disclosure. To simplify the illustration, details of the steering components and visual imaging system have been omitted. The illustration is not drawn to scale. In this embodiment, the optical fiber 140 comprises four cores 144a-144d contained within a single cladding 146. Each core may be single-mode with sufficient distance and cladding separating the cores such that the light in each core does not interact significantly with the light carried in other cores. In other embodiments, the number of cores may vary or each core may be contained in a separate optical fiber. In the embodiments of FIGS. 3 and 4, the fiber cores are arranged with 90° spacing about the center of the fiber 140. In other embodiments, four cores may be arranged with one core in the center of the fiber and three cores spaced at 120° intervals about the center.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065 which is incorporated by reference herein in its entirety.

The shape sensor may provide shape data to the tracking system in the form of strain data. Additionally, strain data may be supplemented with data related to light response, temperature errors, twist errors, or other data that may contribute to determining shape.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local bend radius of the fiber, the radial position of the core with respect to the fiber centerline and the angular position of the core about the core centerline with respect to the plane of fiber bending. For example, strain induced wavelength shifts in regions of the cores containing FBG's located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

In this embodiment of FIGS. 3 and 4, the fiber 140 includes the four optical cores 144a-144d disposed at equal radial distances from and equal angular intervals about the axis of the fiber 140 such that in cross-section, opposing pairs of cores 144a-144c and 144b-144d form orthogonal axes. The sensing locations along the four optical cores are aligned such that measurements from each core are from substantially correlated axial regions along the optical fiber. For example, in one embodiment, each core 144a-144d includes an array of collinear FBG's that are disposed at known positions along the lengths of each core 144a-144d such that the FBG's 144a-d for all four cores 144a-144d are aligned at a plurality of sensor segments 137, including the steerable tip 126. In this embodiment, the fiber 140 is centered at a radial distance D1 from a neutral axis 150 that extends longitudinally through the instrument 120. In alternative embodiments, the fiber 140 may be centered about the neutral axis 150 or located at a different radial distance. In this embodiment, the fiber 140 may be offset from the neutral axis to accommodate other components of the instrument 120 such as cables or other steering components or visualization components (not shown) that may be centered on or clustered about the neutral axis 150. In this embodiment, the neutral axis 150 extends generally along the central axis of the instrument 120. The neutral axis is the axis of the instrument 120 along which no axial strains (due to tension or compression) occur during bending.

A bending of the fiber 140 in one of the sensor segments 137 will lengthen at least one core 144a-144d with respect to the opposing core 144a-144d Interrogation of this length differential along the fiber enables the angle and radius of bending to be extracted. This interrogation may be performed using the tracking system 136. There are a variety of ways of multiplexing the FBG's so that a single fiber core can carry many sensors and the readings of each sensor can be distinguished. Some of the various ways are described in U.S. patent application Ser. No. 13/049,012 which is incorporated by reference herein in its entirety.

In alternative embodiments, fibers with fewer or more cores may be used. Likewise, the fiber cores may be arranged in different patterns, such as, a central core with (axial refers to the fiber orientation, not the spacing) additional cores spaced at angular intervals around the central core. In an alternative embodiment, the instrument body may include an internal channel sized to accommodate the optical fiber and separate it from the steering or visualization components, which themselves may be accommodated through separate channels. In one embodiment, a hollow utility channel may provide access for removable devices including removable surgical instruments, removable steering components, removable visualization components or the like.

When a fiber optic shape sensor is positioned offset from the neutral axis, the fiber is subject to axial tensile and compressive forces during bending which strain all of the fiber cores and may contribute to bending measurement error. Temperature variations in the fiber optic shape sensor alter the cores' index of refraction and create apparent strain that also may contribute to bending measurement error. Temperature variations in the shape sensor may result, for example, from patient body heat, friction, heat generated by components of the steering system, or heat generated by components of the visualization system. Both strain and temperature effects appear as common-mode perturbations to the fibers in the shape sensors. Given that the shape sensor provides the bend information as a differential measurement, under ideal circumstances the strain or temperature common-mode perturbations may have only limited impact, if any. However, in practice, the common-mode rejection ratio of the shape sensor is finite and, due to constructional differences, for example, its fibers may react differently to said common-mode perturbations. As a consequence, an undesired differential bend signal may result and negatively affect the accuracy of the bend measurement. Because the strain due to axial forces may not be distinguishable from the apparent strain induced by temperature variations, it may be difficult to determine the magnitude of the bending measurement error due to axial forces versus temperature. Thus, it may be difficult to correct or compensate for the measurement error that results from axial forces and temperature. The problem is compounded because adjusting compensation to make the shape sensor insensitive to axial forces, may make the sensor increasingly sensitive to temperature and vice versa.

Figure 5:
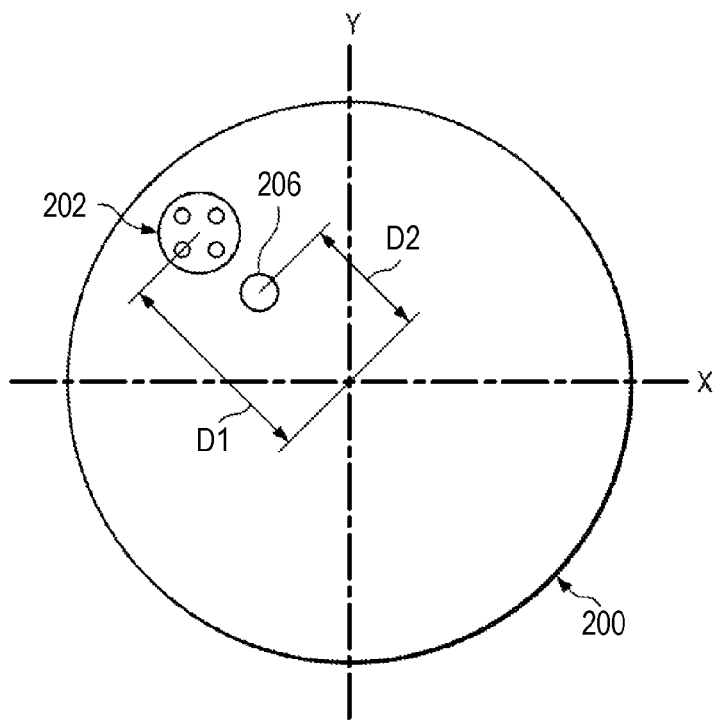
FIGS. 5 and 6 are cross-sectional views of a surgical instrument including an optical fiber shape sensor and a shape sensor compensation device according to another embodiment of the present disclosure.
Figure 6:
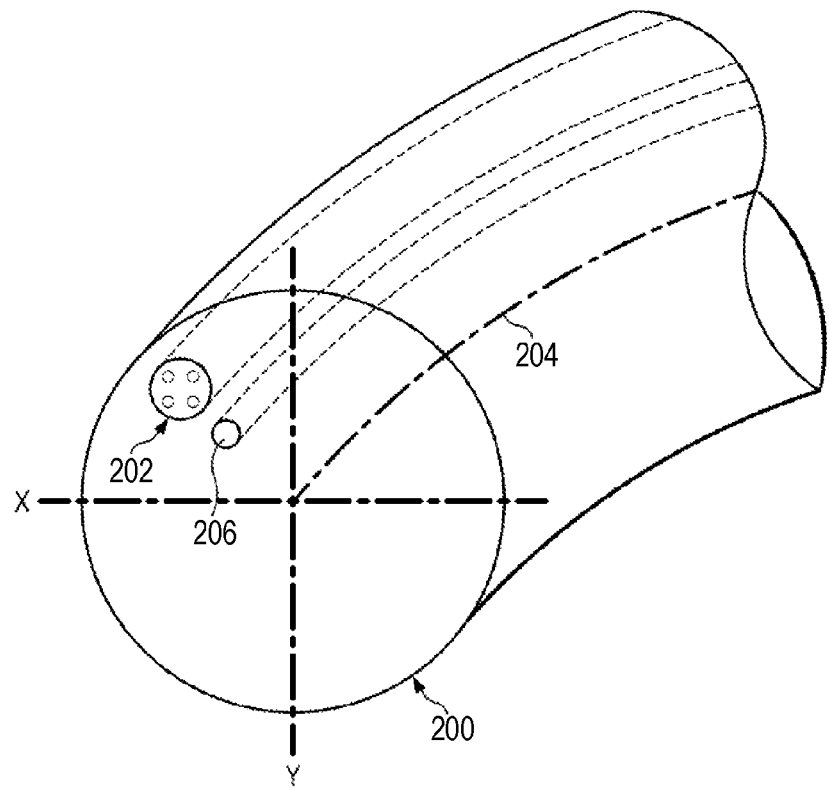

Knowledge about the temperature variations in the instrument near the shape sensor may be used to identify the effects of temperature on the bending measurements and may be used to separate the measurement error caused by temperature from the error caused by axial loading. Information about the effects of the axial forces and the temperature may then be used to algorithmically compensate the computed bending measurements for the instrument. FIGS. 5 and 6 are cross-sectional views of a surgical instrument including an optical fiber shape sensor and a sensor compensation device according to one embodiment of the present disclosure. In this embodiment, an instrument 200 is similar to the instrument 120, with the differences described below. The instrument 200 includes a fiber 202, similar to the fiber 140 which is offset from the neutral axis 204 of the instrument 200 by the distance D1. In this embodiment, the instrument 200 includes a sensor compensation device 206 which measures temperature and/or temperature variations in the instrument 200. The temperature-measuring sensor compensation device 206 is an optical fiber with at least one core. This fiber extends through the instrument 120 generally parallel to the neutral axis 204. The sensor compensation device 206 is centered at a radial distance D2 from a neutral axis 204 of the instrument 200. In this embodiment, the radial distance D2 is smaller than the radial distance D1 and the sensor compensation device 206 is between the neutral axis and the fiber 202. In alternative embodiments, the sensor compensation device may be positioned at a radial distance greater than D1. To accurately determine the effects of temperature on the shape sensor 202, the sensor compensation device may be located anywhere generally near the sensor, within the instrument 200. Optical fiber-based temperature measurement devices may determine temperature or temperature variations in a variety of ways. For example, an optical fiber may be constructed so that temperature modulates the intensity, phase, polarization, wavelength or transit time of light in the fiber. Alternatively, the optical fiber may have evanescent wave loss that varies with temperature, or temperature may be determined by scatter analysis. Knowledge of the temperature or temperature variations within the instrument near the shape sensor may allow for the separation of the effects of temperature and axial forces and for the identification of their effect on bending measurements for the overall instrument 200. Algorithmic compensation techniques are used to remove the effects of temperature and/or axial forces from the final bending measurements. Alternative systems for measuring temperature within the instrument may be also be suitable for use in correcting the effects of temperature from final measurements. Alternative temperature measurement systems may include the use of a plurality of discrete single-point temperature sensors, such as thermocouples, resistance-based temperature sensors, and silicon diodes, at different locations along the instrument. The measurements taken at the different locations may be interpolated.

In some embodiments, compensation for temperature effects on shape sensor 202 can be performed using predetermined characterization data. This temperature characterization data can be generated empirically via controlled application of a temperature gradient(s) (either continuous or localized) to shape sensor 202. By holding shape sensor 202 in a fixed configuration (e.g., straight, or with a known curvature), applying the predetermined temperature gradient (e.g., using individual or continuous heating elements), and monitoring the change in sensor output, the effects of temperature variations on sensor 202 can be characterized. In some embodiments, a single temperature gradient can be applied to shape sensor 202, while in other embodiments, multiple temperature gradients can be applied to shape sensor 202. In any event, the generated temperature characterization data can be compiled in any format, such as a lookup table housing the empirically-generated data, a mathematical model of the thermal response, or a simple scaling factor as a function of temperature, among others. This temperature characterization data can then be provided as a discrete package (e.g., to be stored in or loaded into a computer-readable memory), combined with other sensor-related data (e.g., incorporated into an overall calibration file for sensor 202), or can be integrated into the measurement algorithms/software/hardware for reading the output of sensor 202 (e.g., an interrogator or other electronic system such as tracking system 136).

In an alternative embodiment, the optical fiber temperature sensor may be shrouded in an insulation material together with the fiber shape sensor. The insulation may be used to reduce the effect of external temperature changing sources.

Figure 7:
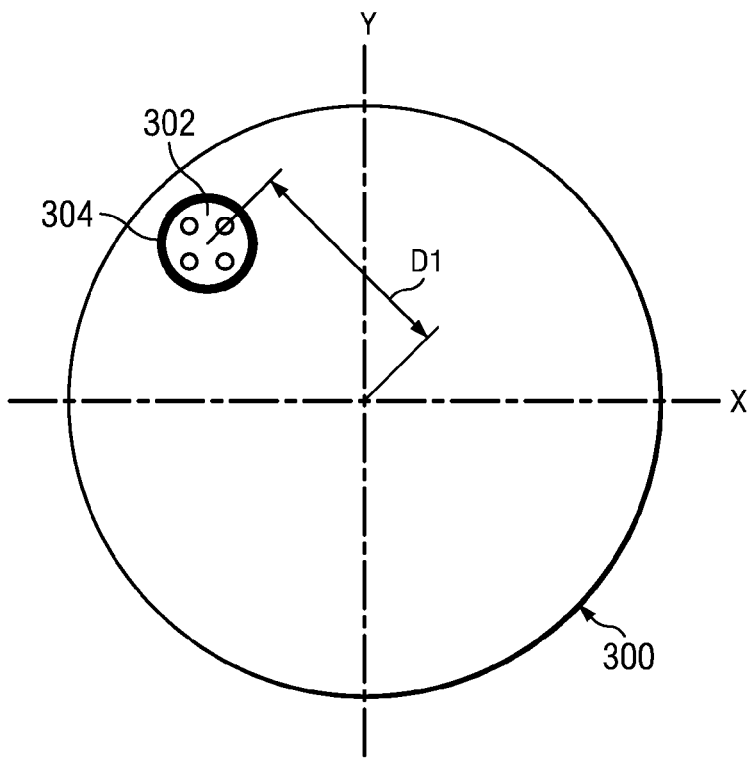
FIG. 7 is a cross-sectional view of a surgical instrument including an optical fiber shape sensor and a shape sensor compensation device according other embodiments of the present disclosure.

FIG. 7 is a cross-sectional view of a surgical instrument including an optical fiber shape sensor and a sensor compensation device according to another embodiment of the present disclosure. In this embodiment, an instrument 300 is similar to the instrument 120, with the differences described below. The instrument 300 includes a fiber shape sensor 302, similar to the fiber shape sensor 140 which is offset from the neutral axis of the instrument 300 by the distance D1. In this embodiment, the instrument 300 includes a sensor compensation device 304 which reduces the temperature variations across the transverse dimensions of the fiber 302. The sensor compensation device 304 may be a highly thermal conductive coating, layer, jacket, or tubing that serves to distribute heat uniformly around and along the optical fiber sensor 302. The sensor compensation device 304 may alternatively be a highly insulating coating, layer, jacket, or tubing that insulates optical fiber sensor 302 from external temperature variations. By maintaining a relatively constant temperature across the fiber shape sensor 302, the sensor compensation device 302 reduces the measurement error that may be caused by high temperatures or temperature variations in the sensor.

Figure 8:
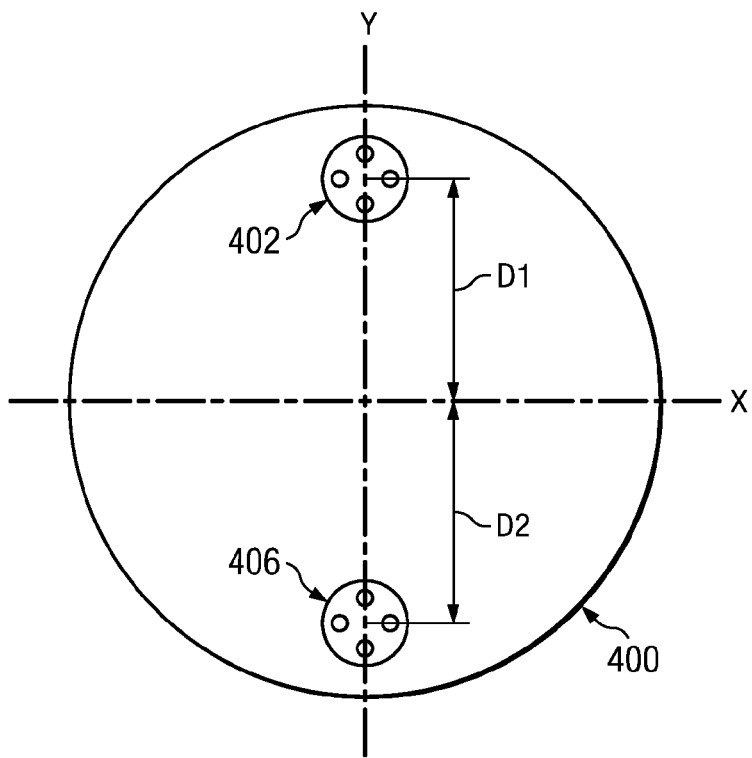
FIGS. 8 and 9 are cross-sectional views of a surgical instrument including an optical fiber shape sensor and a shape sensor compensation device according to another embodiment of the present disclosure.
Figure 9:
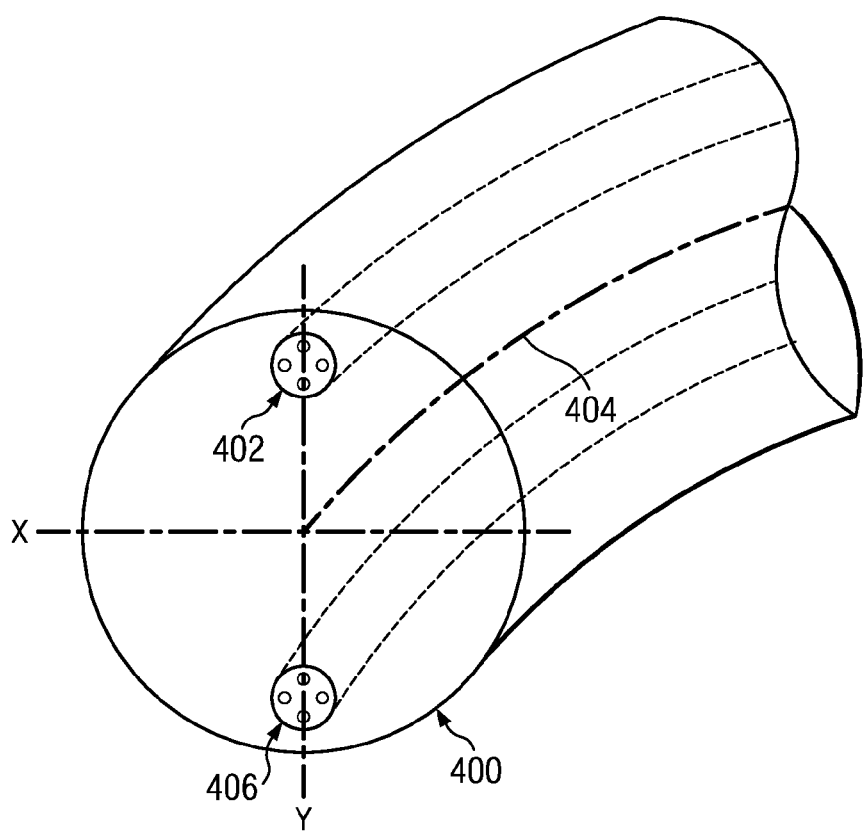

Knowledge about the axial forces causing compression and tension in the shape sensor may be used to identify the magnitude and/or effects of axial forces on the bending measurements and may also be used to separate the measurement error caused by axial forces versus temperature. Information about effects of the axial forces and the temperature may then be used to algorithmically compensate the computed bending measurements for the instrument. FIGS. 8 and 9 are cross-sectional views of a surgical instrument including an optical fiber shape sensor and a sensor compensation device according to another embodiment of the present disclosure. In this embodiment, an instrument 400 is similar to the instrument 120, with the differences described below. The instrument 400 includes a fiber shape sensor 402, similar to the fiber shape sensor 140 which is offset from the neutral axis 404 of the instrument 400 by the distance D1. In this embodiment, the instrument 400 includes an optical fiber sensor compensation device 406 which measures the same bend in the instrument 400 but with different axial forces. The sensor compensation device 406 is an optical fiber identical to or substantially similar to the shape sensor fiber 402.

The sensor compensation device 406 is centered at a radial distance D2 from the neutral axis 404 of the instrument 400, but is positioned on the opposite side of the neutral axis (approximately 180° angular displacement) from the shape sensor fiber 402. In this embodiment, the radial distance D2 is the same as the radial distance D1. In alternative embodiments, the fiber optic sensor compensation device may be positioned within the instrument at other distances from the neutral axis or at other angular displacements from the shape sensor.

When positioned at opposite but equal locations from the neutral axis 404, a bend about the X-axis (bending in the YZ-plane) will place one of the fibers 402, 406 into compression and the other into tension. Thus the bend measurements derived from each of the fibers 402, 406 would exhibit errors due to opposite axial forces. The true value of the bend, at the neutral axis, would be a value between the fiber bend measurements. Knowledge of the axial force measurement error within the instrument may also allow for the separation of the effects of temperature and axial forces and for the identification of their respective effects on bending measurements. Algorithmic compensation techniques are then used to remove the effects of axial forces and/or temperature from the final bending measurements. Although the fiber 402 is identified as the shape sensor and fiber 406 is identified as the shape sensor compensation device, it is understood that because the fibers are operatively the same, either one can be considered the sensor and the other the compensation device.

Figure 10:
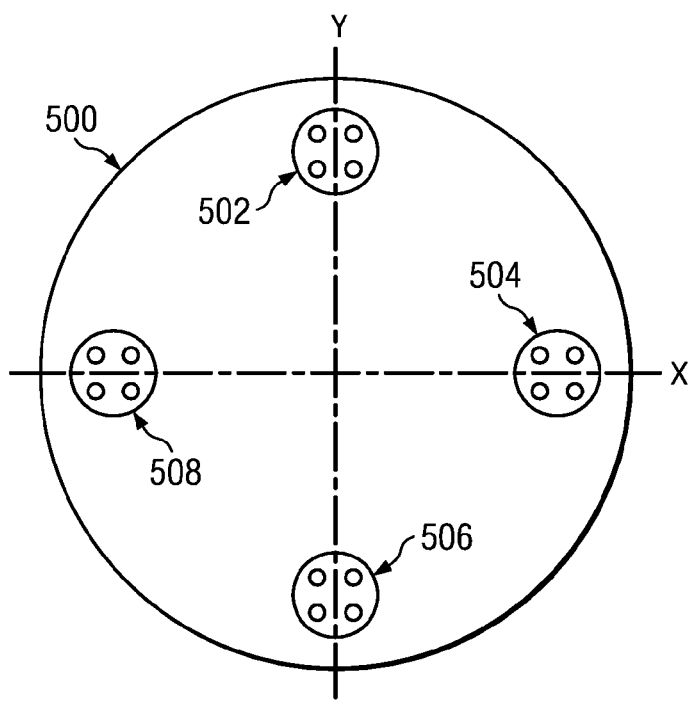
FIG. 10 is a cross-sectional view of a surgical instrument including an optical fiber shape sensor and a shape sensor compensation device according to another embodiment of the present disclosure.

FIG. 10 is a cross-sectional view of a surgical instrument including an optical fiber shape sensor and a shape sensor compensation device according to another embodiment of the present disclosure. In this embodiment, an instrument 500 is similar to the instrument 400 of FIG. 8, but includes a plurality of radially spaced optical fiber shape sensors 502-508, each of which is identical to or substantially similar to shape sensor 140 of FIG. 1. In this embodiment, each shape sensor 502-508 serves as a sensor compensation device to the oppositely positioned sensor. For example, the axial load measurement error associated with shape sensor 504 may be used to compensate the measurements derived from shape sensor 508 and vice versa, to achieve a compensated bend measurement for the neutral axis. Using a plurality of radially spaced optical fiber shape sensors allows for axial force compensation through different bending planes.

Figure 11:
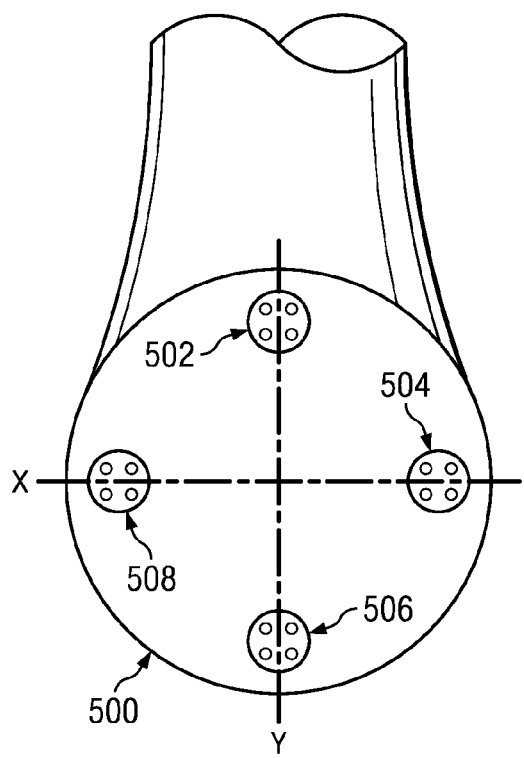
FIGS. 11 and 12 illustrate the surgical instrument of FIG. 10 bent in different planes.
Figure 12:
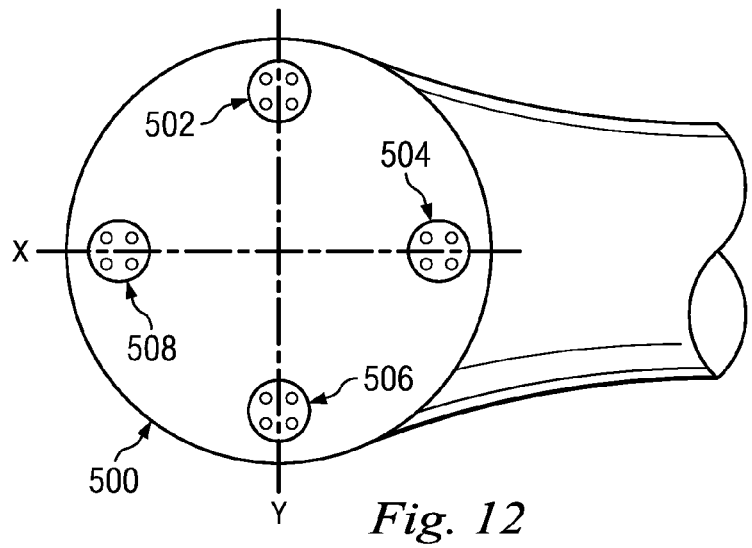

For example, FIGS. 11 and 12 illustrate the surgical instrument 500 of FIG. 10 bent in the YZ and XZ planes, respectively. In FIG. 11, the bend in the YZ plane puts shape sensor 502 into compression and shape sensor 506 into tension. The equal and opposite positions of the shape sensors 502, 506 about the neutral axis will cause equal and opposite axial strains in the sensors. Shape sensors 504, 508 would experience minimal or no axial forces and should provide the same bending measurement. In FIG. 12, the bend in the XZ plane puts shape sensor 504 into compression and shape sensor 508 into tension. The equal and opposite positions of the shape sensors 504, 508 about the neutral axis will cause equal and opposite axial strains in the sensors. Shape sensors 502, 506 would experience minimal or no axial forces. and should provide the same bending measurement. Using a radial array of shape sensors may more accurately reduce the measurement errors due to axial strain for bending in a variety of different planes.

For alternative embodiments in which the instrument is not symmetric about a neutral axis, shape sensor placement about the neutral axis may be calculated according to known methods so that the effects of the axial forces are equal and opposite.

Figure 13:
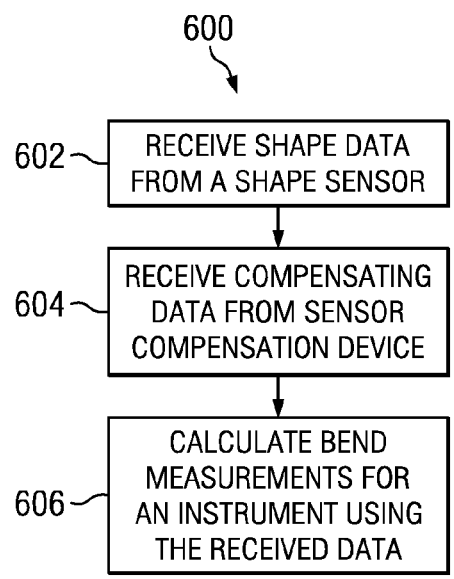
FIG. 13 is a flowchart describing a method according to an embodiment of the disclosure.

FIG. 13 is a flowchart providing a method 600 for using the shape sensing apparatus. Prior to implementation of this method, preoperative images (e.g., CT, MR, or the like) of the patient may be captured. During the surgical procedure, the instrument may be inserted into the patient through a natural or surgically created opening. The display system may display endoscopic images from the visualization system and may also display preoperative images associated with the current location of the tip of the instrument. As the instrument navigates natural or surgically created passageways with the patient, the tracking system and the navigation system are used to determine the bend of various segments of the instrument and thus the overall shape of the instrument. At 602, shape data is received from a fiber optic shape sensor extending within the surgical instrument parallel to the neutral axis of the surgical instrument. At 604, compensating data is received from a sensor compensation device. For example, temperature data may be received from a temperature sensor located near the shape sensor or axial load shape data may be received from another shape sensor located opposite the neutral axis of the instrument from the shape sensor. Optionally, temperature sensor information may be modified or otherwise combined with predetermined temperature characterization data. At 606, a bend measurement for the surgical instrument is calculated using the data received from the shape sensor and the sensor compensation device.

Although the shape sensors and sensor compensation devices have been described herein with respect to teleoperated or hand operated surgical systems, these sensors and sensor compensation systems will find application in a variety of medical and non-medical instruments in which accurate instrument bending measurements would otherwise be compromised by temperature, sensor location, or other physical conditions of the shape sensors.

One or more elements in embodiments of the invention may be implemented in software to execute on a processor of a computer system such as control system 108. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A shape sensing apparatus comprising:
   an instrument including an elongated shaft with a neutral axis;
   a first shape sensor including an elongated optical fiber extending within the elongated shaft at a first radial distance from the neutral axis, wherein the first shape sensor includes a first plurality of optical cores, each of which includes a fiber Bragg grating;
   a shape sensor compensation device extending within the elongated shaft, the shape sensor compensation device including a second shape sensor, wherein the second shape sensor includes a second plurality of optical cores, each of which includes a fiber Bragg grating and wherein the second shape sensor extends within the elongated shaft at a second radial distance from the neutral axis and wherein an angular displacement between the first and second shape sensor about the neutral axis is approximately 180° and the first and second radial distances are approximately equal; and
   a tracking system adapted to receive shape data from the first shape sensor and compensating data from the shape sensor compensation device for calculating a bend measurement for the instrument at the neutral axis.

2. The apparatus of claim 1 wherein the shape sensor compensation device includes a plurality of shape sensors that together with the first shape sensor, are arranged at angular intervals about the neutral axis at the first radial distance.

3. A method of operating a shape sensing apparatus comprising:
   providing an instrument including an elongated shaft defining a neutral axis;
   receiving shape data from a first shape sensor, the first shape sensor including an elongated optical fiber extending within the elongated shaft at a first radial distance from the neutral axis, wherein the first shape sensor includes a first plurality of optical cores, each of which includes a fiber Bragg grating;
   receiving compensation data from a shape sensor compensation device extending within the elongated shaft, the shape sensor compensation device including a second shape sensor, wherein the second shape sensor includes a second plurality of optical cores, each of which includes a fiber Bragg grating and wherein the second shape sensor extends within the elongated shaft at a second radial distance from the neutral axis and wherein an angular displacement between the first and second shape sensor about the neutral axis is approximately 180° and the first and second radial distances are approximately equal;
   generating an instrument bend measurement at the neutral axis based upon the received shape data and the compensation data; and
   displaying a virtual image of the instrument based on the instrument bend measurement.

4. The method of claim 3 wherein the shape sensor compensation device includes a plurality of shape sensors that together with the first shape sensor, form a ring about the neutral axis at the first radial distance and wherein receiving compensation data includes receiving the compensation data from one of the plurality of shape sensors located on a common bending plane with the first shape sensor.

5. A medical instrument system comprising:
   an instrument including an elongated shaft with a neutral axis;
   a first shape sensor including an elongated optical fiber extending within the elongated shaft at a first radial distance from the neutral axis, wherein the first shape sensor includes a first plurality of optical cores, each of which includes a fiber Bragg grating; and
   a shape sensor compensation device extending within the elongated shaft, the shape sensor compensation device including a second shape sensor, wherein the second shape sensor includes a second plurality of optical cores, each of which includes a fiber Bragg grating and wherein the second shape sensor extends within the elongated shaft at a second radial distance from the neutral axis and wherein an angular displacement between the first and second shape sensor about the neutral axis is approximately 180° and the first and second radial distances are approximately equal;
   a tracking system adapted to receive shape data from the first shape sensor and compensating data from the shape sensor compensation device for calculating a bend measurement for the instrument at the neutral axis; and a display system adapted to display a virtual image of the instrument using the bend measurement.

6. The medical instrument of claim 5 wherein the instrument includes an end effector for manipulating tissue in response to a teleoperation command.

7. The medical instrument of claim 5 wherein the shape sensor compensation device includes a plurality of shape sensors that together with the first shape sensor, are arranged at angular intervals about the neutral axis at the first radial distance.

* * * * *